United States Patent
Badawy et al.

(10) Patent No.: US 9,945,812 B2
(45) Date of Patent: Apr. 17, 2018

(54) SIMULTANEOUS ION SENSING AND GAS SAMPLING IN COMBUSTION ENGINE CYLINDERS AND OTHER COMBUSTION SYSTEMS

(75) Inventors: Tamer H. Badawy, Detroit, MI (US); Fadi Estefanous, Warren, MI (US); Naeim A. Henein, Grosse Pointe Shores, MI (US)

(73) Assignee: Wayne State University, Detroit, MI (US)

( * ) Notice: Subject to any disclaimer, the term of this patent is extended or adjusted under 35 U.S.C. 154(b) by 54 days.

(21) Appl. No.: 14/232,645

(22) PCT Filed: Jul. 15, 2011

(86) PCT No.: PCT/US2011/044141
§ 371 (c)(1),
(2), (4) Date: May 5, 2014

(87) PCT Pub. No.: WO2013/012405
PCT Pub. Date: Jan. 24, 2013

(65) Prior Publication Data
US 2014/0232414 A1    Aug. 21, 2014

(51) Int. Cl.
*G01N 27/62*    (2006.01)
*F02D 35/02*    (2006.01)

(52) U.S. Cl.
CPC ........... *G01N 27/62* (2013.01); *F02D 35/021* (2013.01); *G01N 27/626* (2013.01)

(58) Field of Classification Search
CPC ......... H01J 2237/08; H01J 47/02; H01J 49/16
USPC ................................ 324/464, 459, 465, 468
See application file for complete search history.

(56) References Cited

U.S. PATENT DOCUMENTS

| | | | |
|---|---|---|---|
| 3,167,956 A * | 2/1965 | Grey ...................... | G01K 17/10 374/148 |
| 3,384,457 A * | 5/1968 | Norell .................. | G01N 27/626 422/54 |
| 3,445,757 A * | 5/1969 | Krucoff .................. | G01N 30/70 324/464 |
| 3,451,780 A * | 6/1969 | Wise .................... | G01N 27/626 422/54 |
| 3,713,773 A * | 1/1973 | Fontijn et al. ......... | G01N 27/62 250/395 |
| 4,046,012 A | 9/1977 | Studenick | |
| 4,232,545 A | 11/1980 | Dobler et al. | |
| 4,288,749 A | 9/1981 | Murtin | |
| 4,298,795 A * | 11/1981 | Takeuchi ............ | H01J 49/0468 250/282 |
| 4,739,214 A * | 4/1988 | Barr .......................... | 313/362.1 |
| 4,869,094 A | 9/1989 | Kozuka et al. | |

(Continued)

FOREIGN PATENT DOCUMENTS

EP    0 926 338 A1    6/1999

OTHER PUBLICATIONS

Supplementary European Search Report, Application No. EP 11 86 9519, dated Feb. 3, 2015.

(Continued)

*Primary Examiner* — Giovanni Astacio-Oquendo
(74) *Attorney, Agent, or Firm* — Brinks Gilson & Lione

(57) ABSTRACT

A system and method is provided for simultaneous ion current sensing and gas analysis. The system acquires an ion current signal and analyzes the composition of a corresponding gas sample.

20 Claims, 10 Drawing Sheets

(56) References Cited

U.S. PATENT DOCUMENTS

| | | | | |
|---|---|---|---|---|
| 5,153,519 | A | * | 10/1992 | Wentworth et al. ......... 324/464 |
| 5,356,594 | A | * | 10/1994 | Neel .................. G01M 3/20 |
| | | | | 422/54 |
| 5,455,417 | A | * | 10/1995 | Sacristan ............ G01N 27/622 |
| | | | | 250/282 |
| 5,834,629 | A | * | 11/1998 | Hammarberg ........ F02D 35/021 |
| | | | | 73/114.67 |
| 5,889,404 | A | | 3/1999 | Abdel-Rahman et al. |
| 5,922,229 | A | | 7/1999 | Kurano |
| 6,148,660 | A | * | 11/2000 | Chiu .................. F02P 19/028 |
| | | | | 324/378 |
| 6,333,632 | B1 | * | 12/2001 | Yang et al. .................. 324/464 |
| 6,484,709 | B1 | | 11/2002 | Strauss |
| 6,549,013 | B1 | | 4/2003 | Uhl |
| 6,646,253 | B1 | * | 11/2003 | Rohwer ............. H01J 49/0404 |
| | | | | 239/3 |
| 7,960,711 | B1 | * | 6/2011 | Sheehan .............. H01J 49/045 |
| | | | | 250/281 |
| 2002/0060157 | A1 | * | 5/2002 | Calvert ................ C25D 21/12 |
| | | | | 205/82 |
| 2003/0146759 | A1 | * | 8/2003 | Bashkirov ............ G01N 27/64 |
| | | | | 324/464 |
| 2004/0220716 | A1 | | 11/2004 | Yokohata et al. |
| 2008/0040020 | A1 | | 2/2008 | Henein |
| 2009/0099755 | A1 | | 4/2009 | Harbert |
| 2015/0276677 | A1 | * | 10/2015 | Li ........................ G01N 27/62 |
| | | | | 324/464 |

OTHER PUBLICATIONS

International Search Report of PCT/US2011/044141, dated Dec. 6, 2011.

\* cited by examiner

US 9,945,812 B2

SIMULTANEOUS ION SENSING AND GAS SAMPLING IN COMBUSTION ENGINE CYLINDERS AND OTHER COMBUSTION SYSTEMS

GOVERNMENTAL RIGHTS

This invention was made with government support under P.O. No. 085 P7200178 "Development of Synthetic Fueled Generator Sets for Homeland Security" awarded by State of Michigan MEDC, WSU Index 338554. The government may have certain rights in the invention

CROSS-REFERENCE TO RELATED APPLICATIONS

The present application is a National Phase Application of PCT Application No. PCT/US2011/044141, filed Jul. 15, 2011, the content of which is hereby incorporated by reference in its entirety.

BACKGROUND

1. Field of the Invention

The present invention relates to simultaneous ion current sensing and gas sampling in a combustion system.

2. Description of Related Art

Ion current sensors have been used to characterize combustion in different systems. These sensors may be used to identify various stages in the combustion cycle and may also be used to provide information about the output of the combustion process.

SUMMARY

A system and method are provided for simultaneous ionization sensing and gas sampling in a combustion system. The combustion system can be, but is not limited to, reciprocating engines such as spark ignition engines, compression ignition engines and Homogenous charge compression ignition engines, gas turbines, boilers and furnaces. The system is a device that can be used for gas sampling and ion current sensing. The apparatus can be used for research purposes in any of the combustion systems. The device may also be used in the research and development of different combustion systems before production. Further, the device can be used in research to study the details of the auto ignition and combustion processes and develop correlations between the ion current and the composition of the sampled gases at different stages of combustion. This device could be used to build models that get an input from the ion current signal only or from the ion current signal and a gas analyzer to predict certain combustion and emission characteristics. These models can be used in any combustion system with the feedback from the ion current sensor to control, for example, one or more operating parameters in an internal combustion engines, gas turbines, boilers and furnaces to meet stringent emission regulations and improve performance and fuel economy.

Further objects, features and advantages of this application will become readily apparent to persons skilled in the art after a review of the following description, with reference to the drawings and claims that are appended to and form a part of this specification.

BRIEF DESCRIPTION OF THE DRAWINGS

Aspects of this application will be described by way of examples with reference to the accompanying drawings. They serve to illustrate several aspects of the present application, and together with the description provide explanation of the system principles. In the drawings.

DETAILED DESCRIPTION

Figure 1:
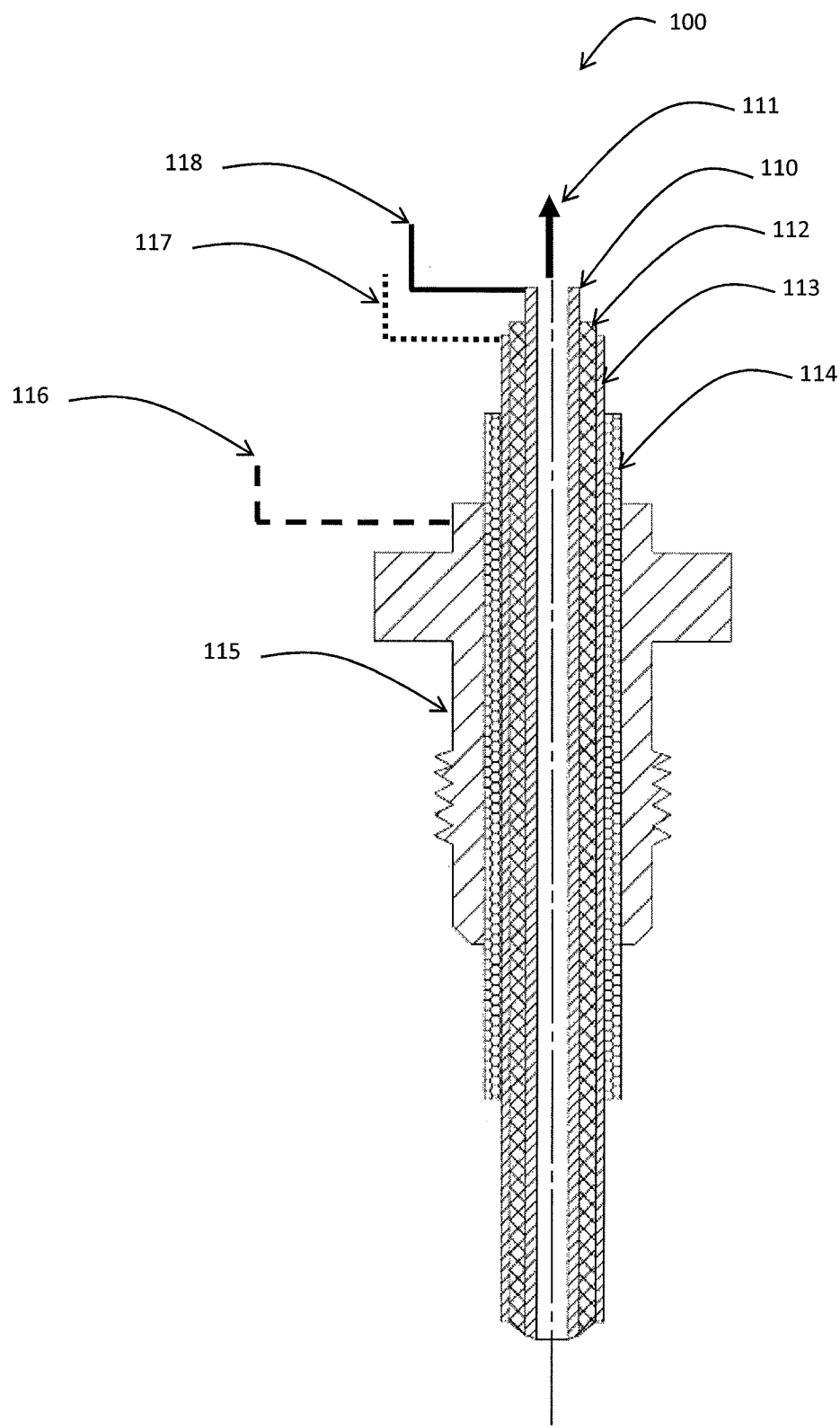
FIG. 1 is schematic of a probe configuration for simultaneous ion sensing and gas sampling

Currently, there are no sensors that determine the correlation between chemical products developed during combustion and ion current signal. For example in internal combustion engines, combining in-cylinder sampling techniques with ion current detection may be of great importance in understanding how ionization processes are tied to different combustion processes, and thus create new methods to control internal combustion engines under various operating modes and fuels. Ion-sensors are local sensors; they can only measure current created by species ionized in the vicinity of the sensor. Therefore, in-cylinder gas sampling probes and ion sensors may be improved by measuring their signals at the same exact location in order to study the effect of different sampled species on the ionization signal.

According to this application, an in-cylinder gas sampling probe has been made to accommodate ion current measurements. The new in-cylinder gas sampling/ion-current probe helps to identify the effect of various species on the ion current signal with respect to amplitude and shape. This sensor can accurately determine the contribution of the in-cylinder sampled species on the ionization signal. Species such as NOx, CO, $CO_2$, and hydrocarbons produced inside the combustion chamber throughout the engine cycle are of great importance to understand the combustion behavior at different engine operating conditions. Combining in cylinder sampling techniques with ionization measurement is of great value in internal combustion engines research and development, which is needed to meet stringent emission standards. This invention will results in a better understanding of the ionization processes in both gasoline and diesel engines and their operation under different regimes including homogenous charge compression ignition (HCCI) while using conventional, alternative, and renewable fuels. This improvement in the sampling probe was initially created to validate the results of a detailed investigation on the sources of ionization in internal combustion engines and the contribution of species such as NOx, CO, $CO_2$, or hydrocarbons in this process. Researchers and scientists will be able to understand details of combustion, $NO_x$ and other species formation in different types of combustion systems using this technology. This will help in the development of different improved control strategies for these systems to meet stringent emission standards. In addition, this device can be used as a combustion diagnostics tool in different combustion systems and as a combustion indicator.

In achieving a prototype unit, an in-cylinder gas sampling probe is modified to sense ion current as discussed above. A high temperature coating may be used to cover and insulate the sampling tube electrically from the rest of the engine body. A glow plug adapter may be used as an outer sleeve to fit the sampling probe in the glow plug hole of the cylinder head in a diesel engine. The probe can also be fitted in a special sleeve that can be introduced in the combustion chamber, a spark plug of a gasoline or HCCI engine, a gas turbine, boiler and furnace.

The modified probe may be connected to an ionization circuit. A DC power supply with preset positive potential may be used to supply power to the probe. It should be noted that the ionization circuit could operate on a positive polarity or negative polarity. The positive polarity is the configuration of terminals shown in FIG. 4, where the sampling tube is connected to the positive terminal and the outer sleeve is connected to the negative terminal of the power supply. The negative polarity is the configuration of terminals, where the sampling tube is connected to the negative terminal and the outer sleeve is connected, to the positive terminal of the power supply. The voltage drop is measured across a resistor placed in the circuit. The voltage acquired is amplified using a signal conditioning unit and recorded for further analysis.

Figure 7:
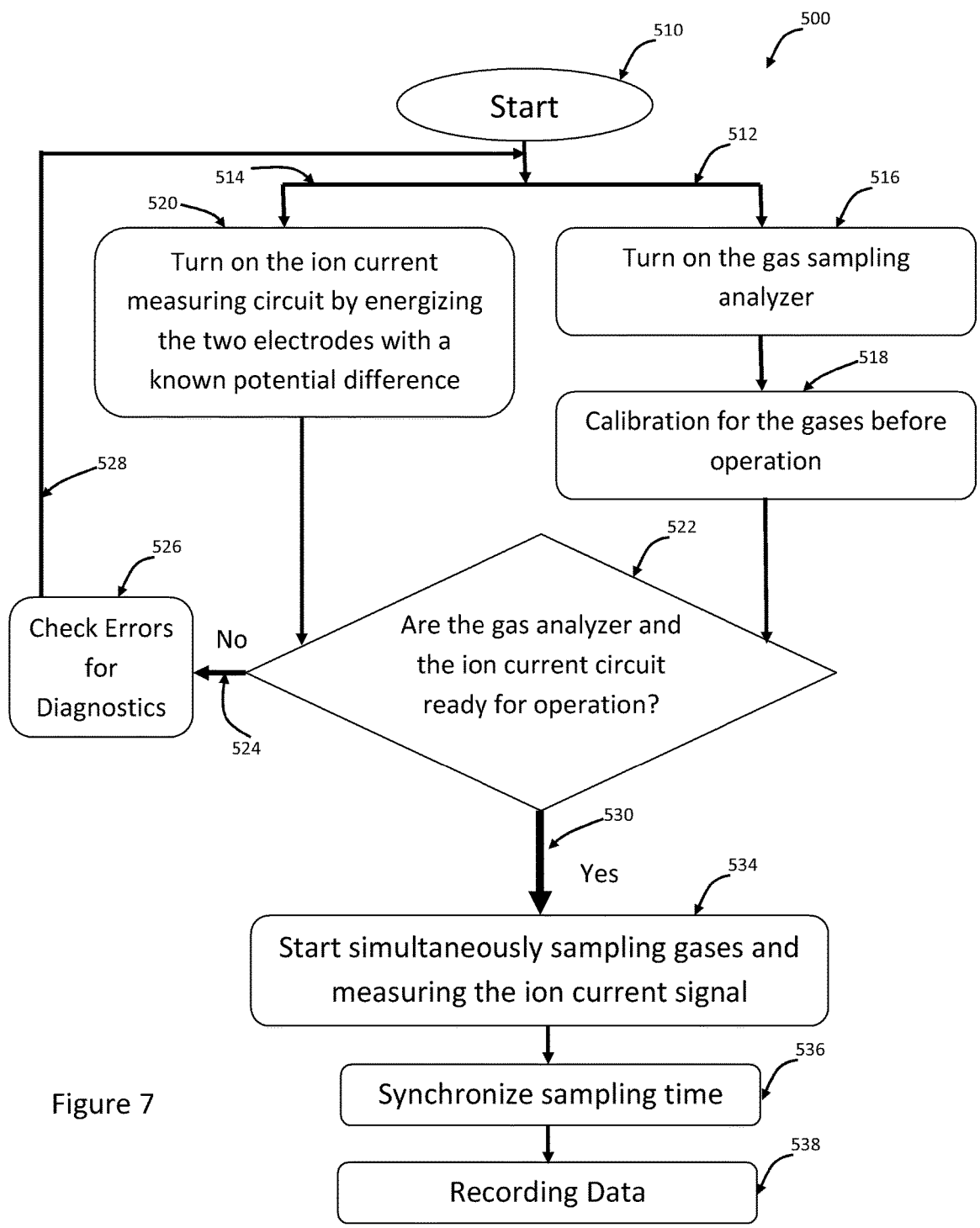
FIG. 7 is flowchart illustrating a method for simultaneous ion current sensing and gas analysis.

Operation of the prototype sensor in order to extract gases from the engine cylinder and to sense ion current is discussed in the flowchart of FIG. 7. Two paths are provided, one is for gas sampling and the other is for ion sensing. The sampling tube may be fitted inside the engine cylinder through the glow plug hole. Gas may be sampled via the probe into a gas analyzer and then to a data acquisition system. At the same time, the ionization may be measured at the tip of the gas sampling probe using the ion current circuit discussed above and then the data can be provided to the same data acquisition system. Although, it is understood that other gas analysis devices may be used including gas analysis integrated circuit chips in any of the implementation described herein.

Now referring to FIG. 1, a sampling probe is provided and denoted by reference numeral 100. The sampling probe 100 includes a tube 110 with an opening that is configured to receive gas for analysis. An inner tube 110 is used to deliver the gases to the gas analyzer 111. The inner tube 110 is covered with a heater 112 to maintain the gas at its sampled temperature for accurate measurements. The heater 112 is placed between the inner gas sampling tube 110 and an outer tube 113. The probe 100 may also include an insulator 114 located around the tube 113. In some implementations, the insulator 114 may be a ceramic coating or paint that surrounds the outer tube 113 and prevents electrical connectivity between the tube 113 and the sleeve 115. The tube 113 and sleeve 115 may be comprised of a conductive material such as a metal. In some implementations, the sleeve 115 may be an adapter configured to mount the probe 100 into a glow plug or a spark plug opening of a combustion engine. Further, the probe 100 may be configured to connect the inner tube 110 to a gas analyzer. In addition, the probe 100 may include a cable 118 to connect the heater 113 to a power source to maintain the temperature of the sampled gas. The probe 100 may also be configured to provide an electrical signal from the tube 113 to an ion current circuit configured to sense the ion current from the tip of the tube 113. In the positive polarity of the ion current circuit, a positive terminal is connected to the tube 113 through a wire 117 and a negative terminal is connected to the sleeve 115 through a wire 116. Accordingly, the opening for receiving gases 110 and the tip of the tube 113 are co-located providing the ability to correlate the gas analysis and ion current sensing to the gas sample at the same location within the combustion chamber.

Figure 2:
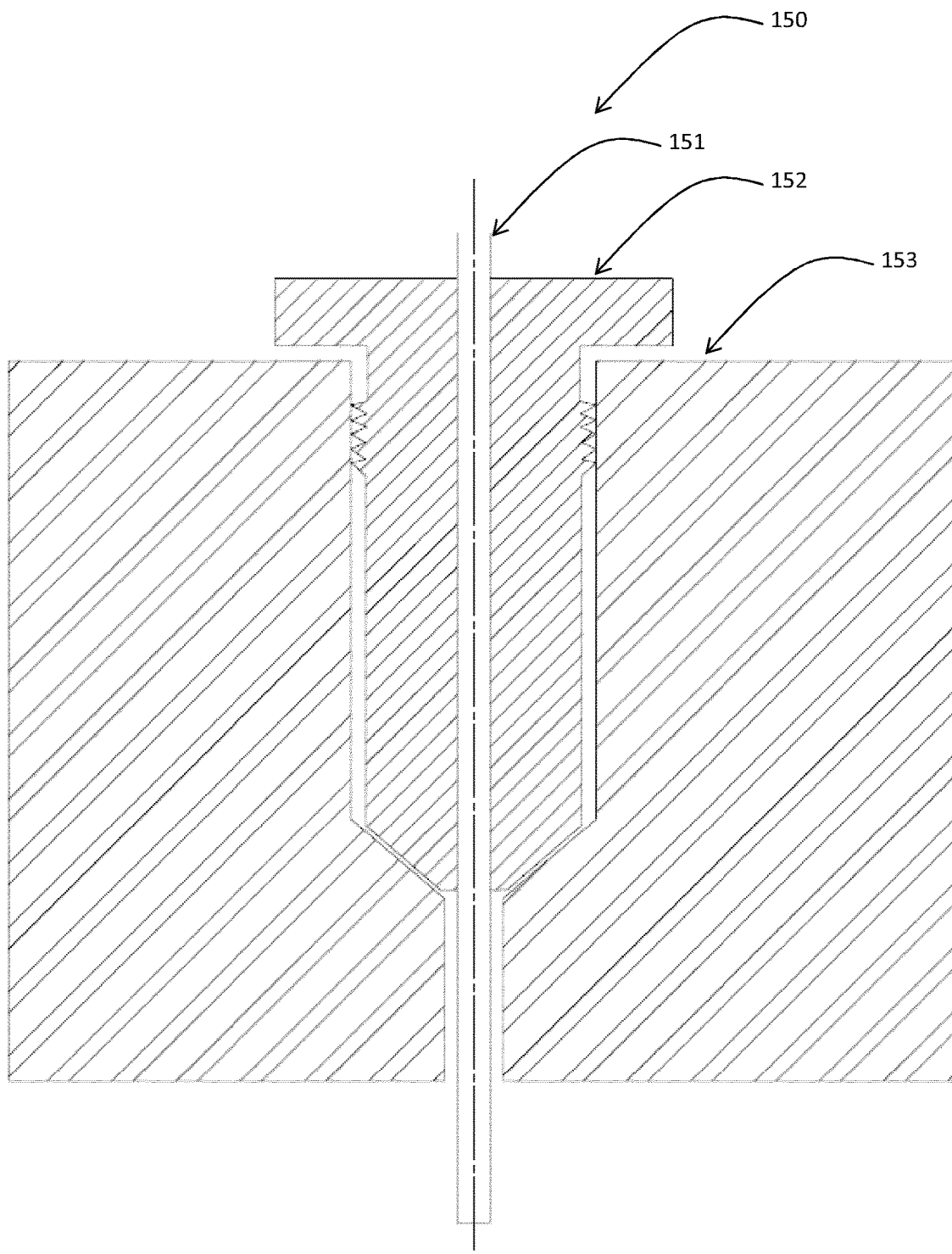
FIG. 2 is schematic of a probe configuration for simultaneous ion sensing and gas sampling

Now referring to FIG. 2, another design for the simultaneous ion sensing and gas sampling is provided and denoted by reference numeral 150. The sampling probe 150 includes a tube assembly 151 with an opening that is configured to receive gas for analysis. The tube assembly 151 may include one or more of an inner tube to deliver the gases to the gas analyzer, a heater to maintain the gas at its sampled temperature for accurate measurements, and an outer tube around the heater. In this design, the sleeve 152 is comprised of an electrically insulated material. The sleeve 152 may be installed in to a combustion system through a various assembling design, for example, but not limited to fastening. The electrically insulated sleeve 152 prevents electrical connectivity between the tube 113 and the combustion system enclosure 153. The combustion system enclosure 153 may be cylinder head in internal combustion engines, combustion wall in gas turbines, and enclosure of boilers or furnaces. Further, the probe 151 may be configured to connect the inner tube to a gas analyzer. In addition, the probe 151 may also be configured to provide an electrical signal from the tube 151 to an ion current circuit configured to sense the ion current from the tip of the tube 151. In the positive polarity of the ion current circuit, a positive terminal is connected to the tube 151 through and a negative terminal is connected to the combustion enclosure 153. Accordingly, the opening for receiving gases 151 and its tip are co-located providing the ability to correlate the gas analysis and ion current sensing to the gas sample at the same location within the combustion chamber.

Figure 3:
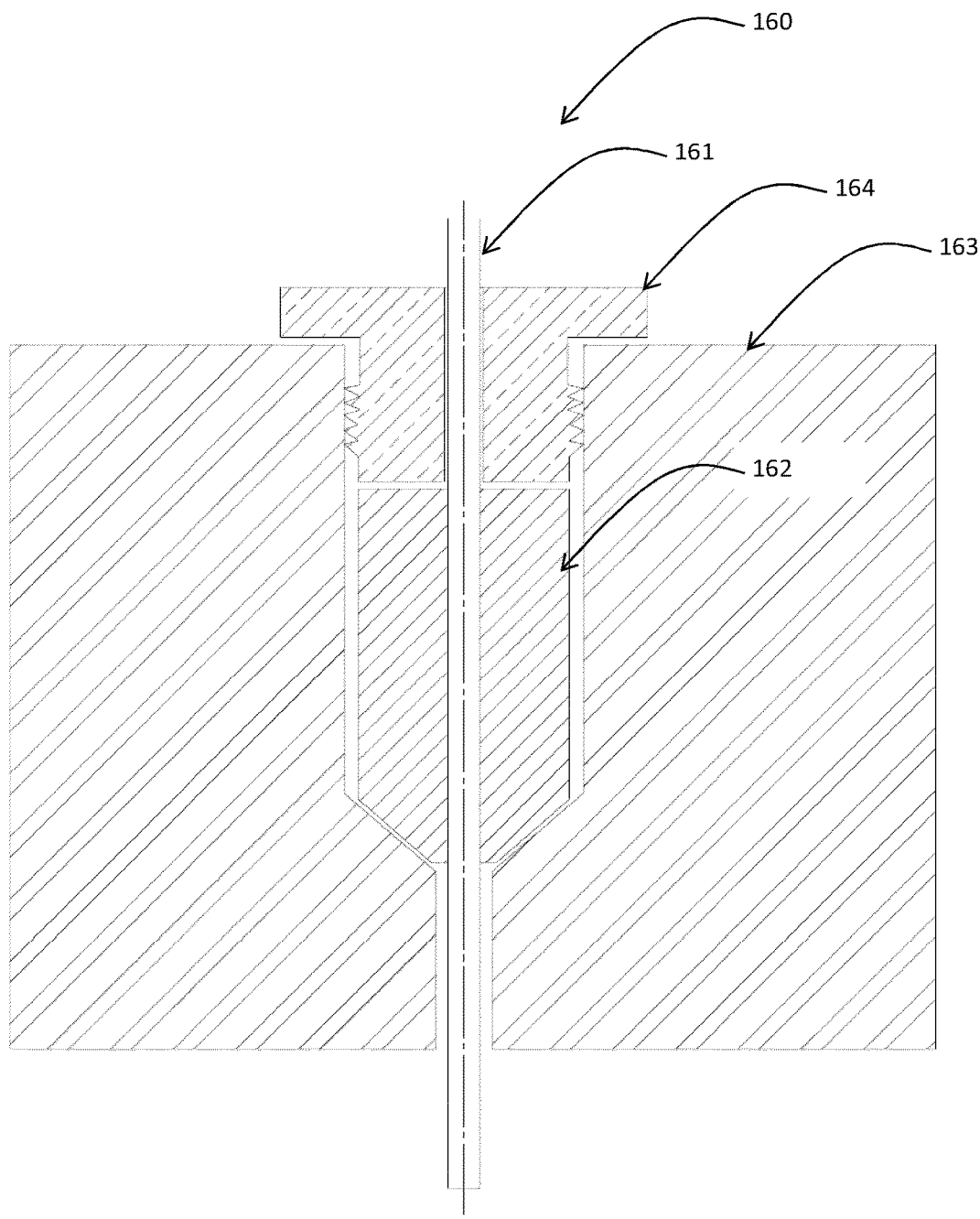
FIG. 3 is schematic of a probe configuration for simultaneous ion sensing and gas sampling

Now referring to FIG. 3, different assembly for the simultaneous ion sensing and gas sampling is provided and denoted by reference numeral 160. The sampling probe 160 includes a tube 161 with an opening that is configured to receive gas for analysis. The tube 161 may include an inner tube to deliver the gases to the gas analyzer, a heater to maintain the gas at its sampled temperature for accurate measurements, and an outer tube around the heater. In this design, the sleeve 162 is comprised of an electrically insulated material. The sleeve 162 may act as a spacer for sealing and electric insulation purposes into a combustion system 163. A locking cap 164 may be used to assemble the sampling probe into the combustion system 163 through a various assembling design for example but not limited to fastening. The electrically insulated sleeve 162 prevents electrical connectivity between the tube 161 and the combustion system enclosure 163. The sleeve 162 may also be designed to electrically insulate the tube 161 from the locking cap 163. The combustion system enclosure 163 may be a cylinder head in internal combustion engines, combustion wall in gas turbines, and enclosure of boilers or furnaces. Further, the probe 161 may be configured to connect the inner tube to a gas analyzer. In addition, the probe 161 may also be configured to provide an electrical signal from the tube 161 to an ion current circuit configured to sense the ion current from the tip of the tube 161. In the positive polarity of the ion current circuit, a positive terminal is connected to the tube 161 through and a negative terminal is connected to the combustion enclosure 163 or the locking cap 164. Accordingly, the opening for receiving gases 161 and its tip are co-located providing the ability to correlate the gas analysis and ion current sensing to the gas sample at the same location within the combustion chamber.

Figure 4:
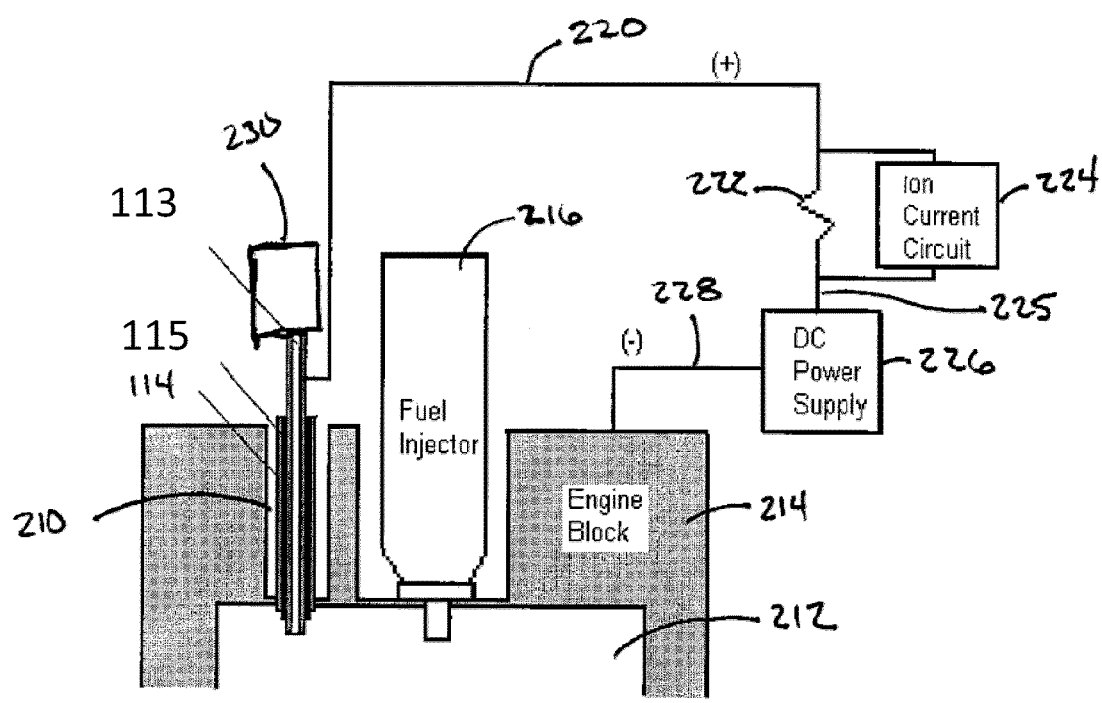
FIG. 4 is sectional side view of a sensing probe installed in a combustion engine.

Now referring to FIG. 4, one implementation of the sampling probe 100 is provided in conjunction with a combustion engine. The tube 113 extends into the combustion chamber 212 formed by the engine block 214. The insulator 114 is located between the tube 113 and the sleeve 115, thereby preventing electrical connectivity between the tube 113 and the sleeve 115. The sleeve 115 may be configured to mount within a glow plug opening 210. For example, the sleeve 115 may include threads or other fastening details that allow the sleeve 115 to engage the engine block 214. As the fuel injector 216 provides fuel to the engine, a piston compresses the fuel causing combustion. It may be beneficial to analyze the gases within the combustion chamber 212 during various phases of the combustion cycle. The analysis of the gases may be used for understanding the combustion process and developing strategies to optimize engine performance. Similarly, the ion current signal may also be used for understanding the combustion process in the engine and optimize engine performance. Further, it may be useful to correlate gas compositions to ion current and/or optimize engine parameters based on the combination of both the gas composition and ion current sensing. As such, the co-location of the gas sampling and ion current sensing may be particularly useful in this regard.

An application for using the ion current circuit may be configured to a positive polarity, where the tube 113 may be connected to a positive ion current lead 220. The positive ion current lead 220 may be connected to a resistor 222 and an ion current circuit 224. The second side of the resistor 222 may be connected to another input of the ion current circuit 224 and the positive lead of a DC power supply as denoted by reference numeral 225. A negative lead 228 of the DC power supply 226 may be connected to the engine block 214 which may be used as a ground return with ion current signal. Accordingly, the DC power supply 226 provides a voltage to the resistor 222. Electric current flows through the resistor 222 depending on the current produced locally between the tube 113 and the engine block 214 in the combustion chamber 212. A current then returns to the DC power supply 226 to complete the circuit through lead 228. To sense the current through the resistor 222, the ion current circuit 224 may be connected in an electrically parallel connection with the resistor 222. The ion current circuit 224 may be connected to a processing unit to collect and analyze the ion current data. The gas received by the inner tube 110 may be provided to a gas analyzer 230. The data from the gas analyzer 230 may be provided to a processing unit in the similar manner to the ion current circuit 224. Accordingly, synchronization of the gas data and ion current data may occur within the processing unit and further analysis based on both the ion current and gas analysis data may be performed by the processing unit.

Figure 5:
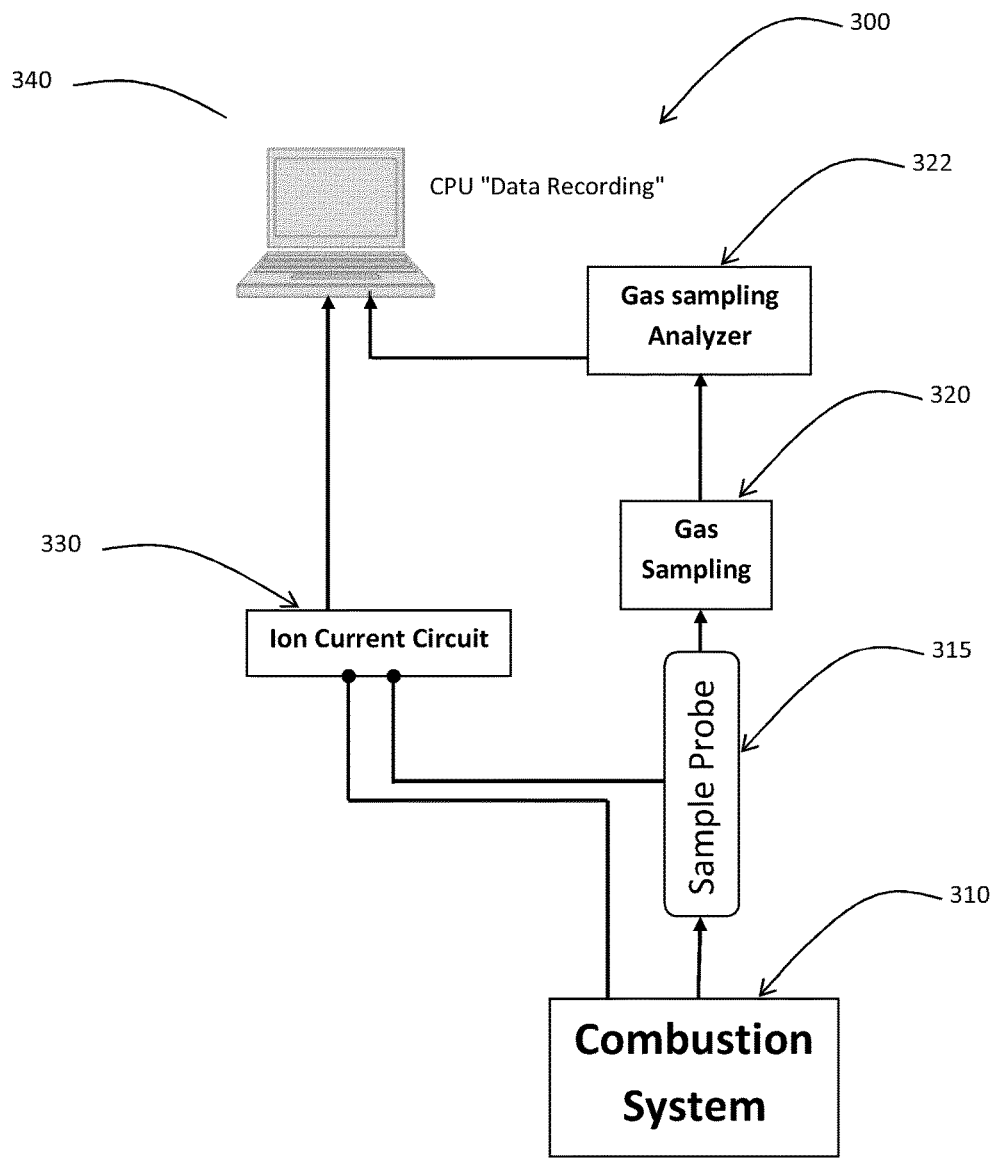
FIG. 5 is a block diagram illustrating a system for simultaneous ion current sensing and gas analysis in any combustion system.

Now referring to FIG. 5, a block diagram of a system for simultaneous ion current sensing and gas sampling is provided. For example, the combustion system 310 may perform a combustion process allowing gas sampling to occur as noted by block 320. The sample probe 315 comprises of simultaneous ion sensing and gas sampling probe. The sampled gas 320 is provided through probe 315 to a gas analyzer as noted by block 322. At the same time, the ion current circuit 330 may be in communication with the combustion system through the probe 315 to identify an ion current signal that is received at the same gas sampling location. The ion current circuit 330 may provide the ion current data to a processing unit 340 in conjunction with the gas sampling data from the gas sample analyzer 322. The processing unit 340 may store the gas sampling data and ion current data in a storage device such as a memory or mass storage unit where the data may be indexed according to a common key such as time or a combustion system characteristic such as the crank angle of a combustion engine. The processing unit 340 may then synchronize the gas analysis and ion current data according to an event or pattern matching in both data sets and/or based on a calibration procedure configured to detect any lag between the ion current and the gas sampled data.

Figure 6:
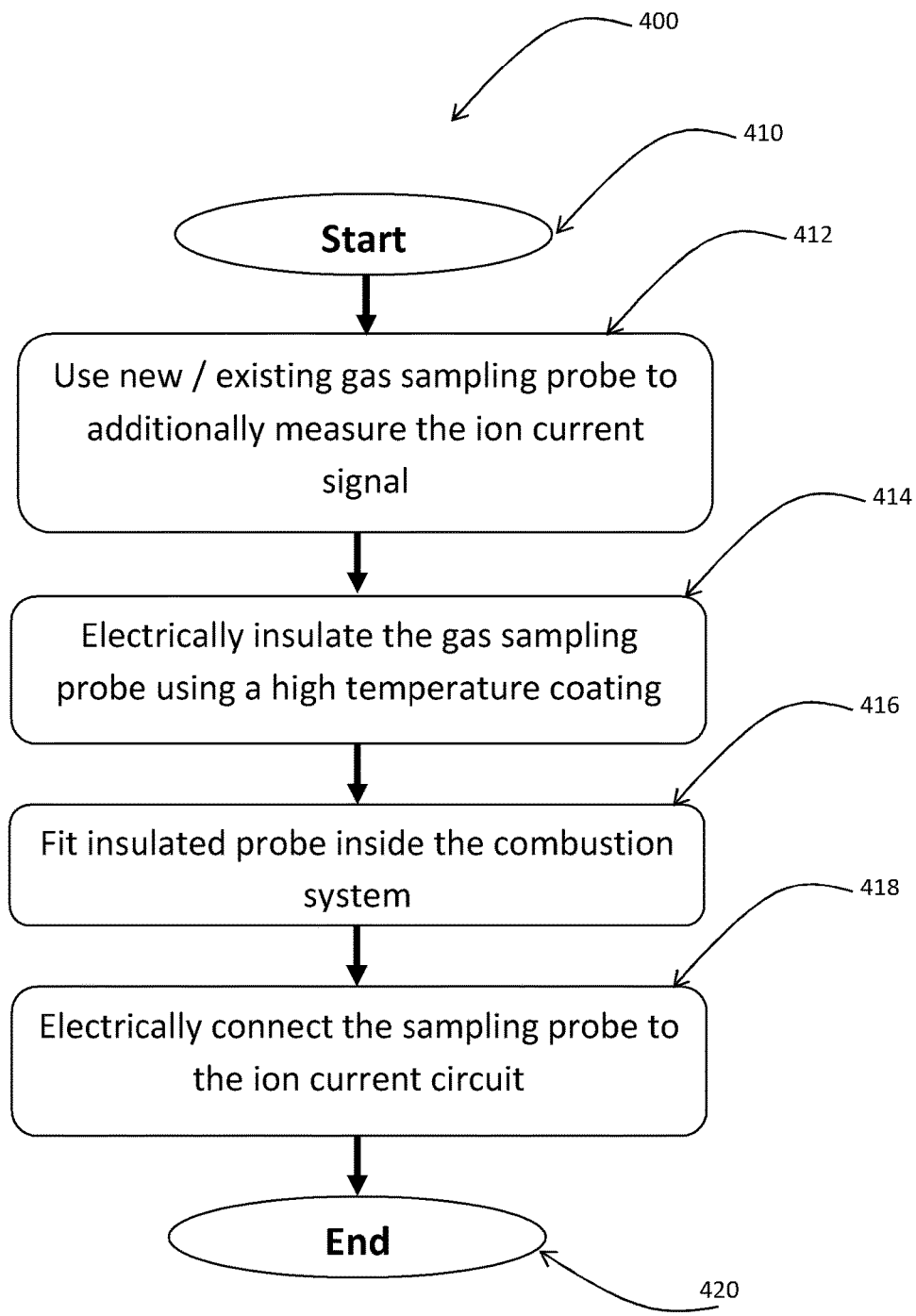
FIG. 6 is flowchart illustrating a method to redesign a new or existing gas sampling probe for simultaneous ion current sensing and gas sampling.

Now referring to FIG. 6, a method 400 is provided producing a sampling probe. The method starts in block 410 and proceeds to block 412. In block 412, a conductive tube is provided. The tube may be a new or existing gas sampling probe having conductive properties also allowing it to receive an ion current signal. In block 414, an electrical insulator is provided over the tube. For example, the tube or gas sampling probe may be insulated using a high temperature ceramic coating. In block 416, the insulated tube may be located within a sleeve, such as an adapter which may be configured based on the application and the type of combustion system. In one example, the sleeve may be a glow plug adapter sleeve configured to mount within a combustion engine. In block 418, the tube may be connected to the ion current circuit. The method ends in block 422.

Now referring to FIG. 7, a method 500 is provided for simultaneously sampling gases and measuring an ion current signal. The method starts in block 510. The method then proceeds along concurrent branches as denoted by lines 512 and 514. Accordingly, the ion current sensing and gas sampling occurs simultaneously as noted by the two branches. Now referring to block 516, the gas sampling analyzer is turned on. In block 518, calibration for gases occurs before operation. At the same time, the ion current measuring circuit is turned on by energizing two electrodes with a known potential difference, as denoted in block 520. When both branches are completed, the method continues to block 522. The system determines if the gas analyzer and ion current circuit are ready for operation. If the gas analyzer circuit and ion current circuit are not ready for operation, the method follows line 524 to block 526. In block 526, the system performs diagnostics to check for errors. If possible, any errors are corrected and the method follows line 528 where the method continues through lines 512 and 514, as described above. Referring again to block 522, if the gas analyzer and ion current circuit are ready for operation, the method follows line 530 to block 534. In block 534, the system simultaneously samples gases and measures the ion current signal. In block 536, the system may synchronize the gas sampling and the ion current signal. As previously mentioned, this may be done by pattern matching or through a calibration technique. Further, it is noted that synchronization of the sampling may only be required with slow response gas sampling devices and with faster technology real time analysis may be possible. In step 538, the data is recorded by the processing unit for further correlation or analysis and/or as a buffer for immediate processing to control engine operating parameters in a feedback loop.

Figure 8:
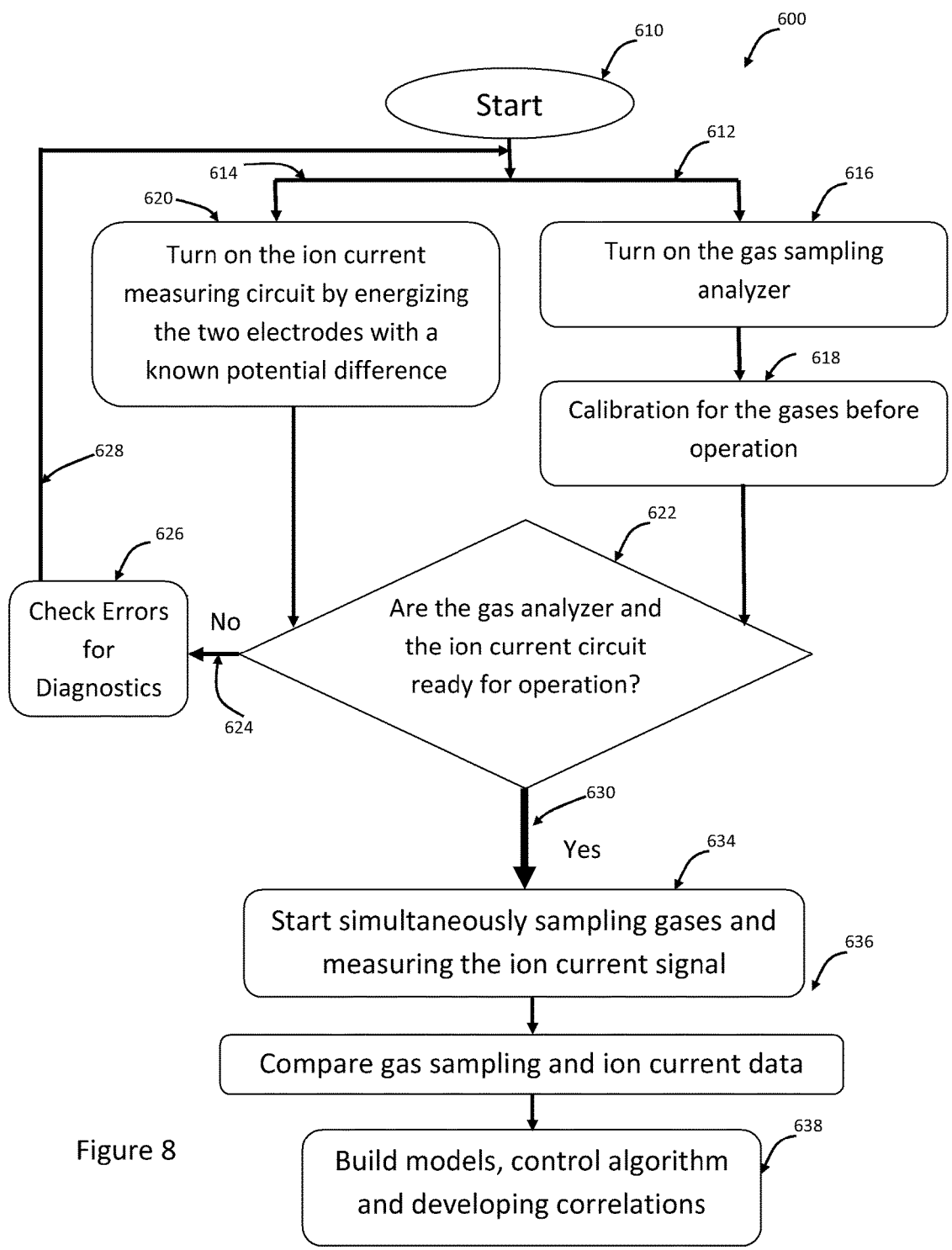
FIG. 8 is flowchart illustrating a method for correlating ion current data and gas analysis data.

Now referring to FIG. 8, a method 600 is provided for simultaneously sampling gases and measuring an ion current signal. The method starts in block 610. The method then proceeds along concurrent branches as denoted by lines 612 and 614. Accordingly, the ion current sensing and gas sampling occurs simultaneously as noted by the two branches. Now referring to block 616, the gas sampling analyzer is turned on. In block 618, calibration for gases occurs before operation. At the same time, the ion current measuring circuit is turned on by energizing two electrodes with a known potential difference, as denoted in block 620. When both branches are completed, the method continues to block 622. The system determines if the gas analyzer and ion current circuit are ready for operation. If the gas analyzer circuit and ion current circuit are not ready for operation, the method follows line 624 to block 626. In block 626, the system performs diagnostics to check for errors. If possible, any errors are corrected and the method follows line 628 where the method continues through lines 612 and 614, as described above. Referring again to block 622, if the gas analyzer and ion current circuit are ready for operation, the method follows line 630 to block 634. In block 634, the system simultaneously samples gases and measures the ion current signal. In block 636, the system may compare gas sampling and ion current data. The comparison may be done subsequent to the measurements or in real time. In block 638, correlations may be build between the ion current data and the gas sampling data. As such, mathematical relationships may be determined to describe the relationship between the gas composition measurements and the ion current data. As such, the information may be used to infer gas composition information from the ion current data. The mathematical relationships may be general relationships or may be a series of relationships identified according to certain engine operational parameters. Further, the correlations may be used for modeling validation and developing control algorithms.

Figure 9:
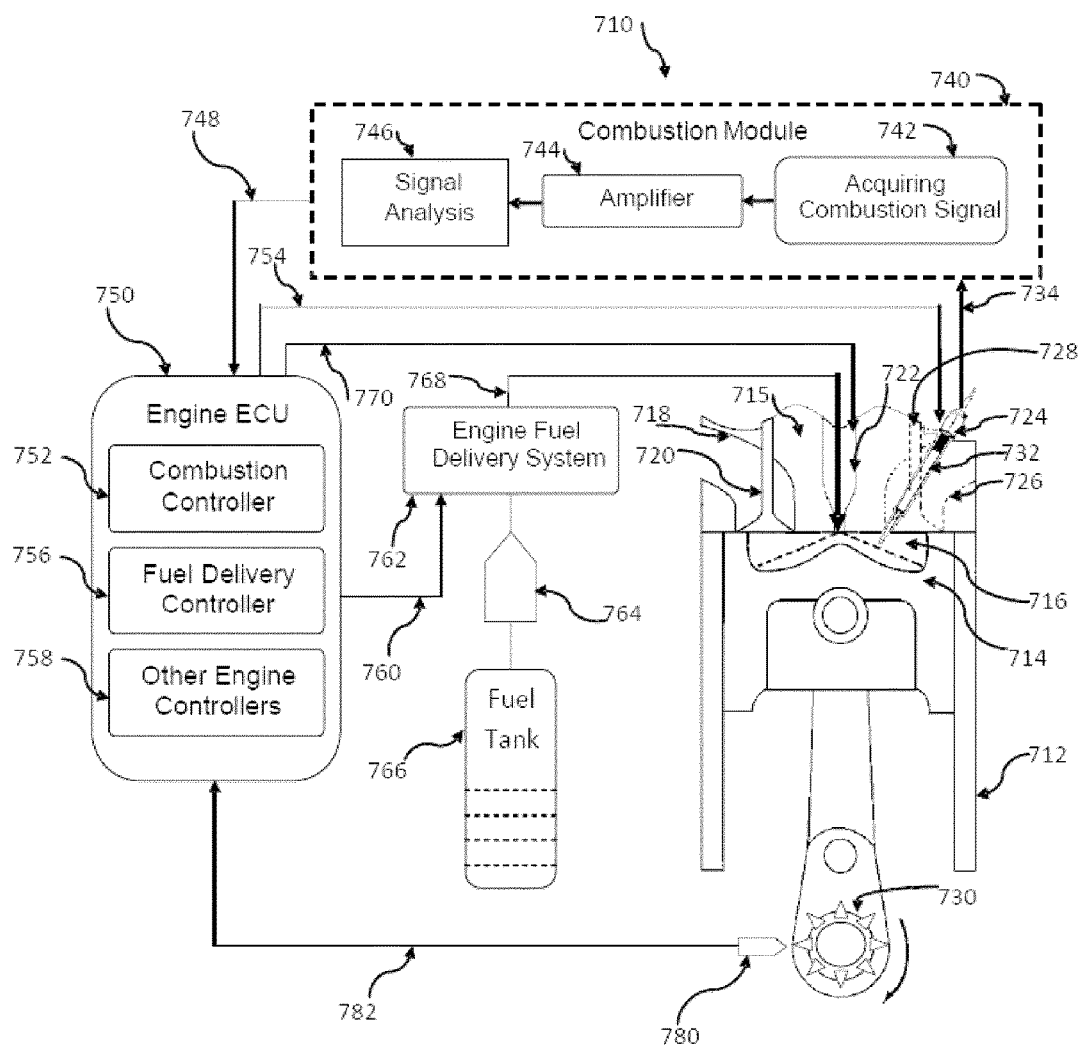
FIG. 9 is a schematic view of a diesel engine.

Now referring to FIG. 9, a schematic view of a diesel engine 710 is provided. For illustrative purposes the schematic shows a single cylinder of an engine, however, it is readily understood that multiple cylinders may be used in combination to form the engine. The cylinder 712 houses piston 714 allowing for reciprocating motion of the piston 714 within the cylinder 712. The combustion chamber 716 is formed by the cylinder houses 712, the piston 714, and the cylinder head 715. Air, a mixture of air and exhaust gases, or other mixtures of any fluid may be provided into the chamber 716 through an intake manifold 718. The flow of air or mixtures made through the intake manifold 718 may be controlled by intake valve 720. Fuel may be provided into the chamber by a fuel injector 722. A glow plug 724 may be used to facilitate the ignition of the fuel inside the combustion chamber 716 causing reciprocating motion of the piston 714. After combustion, the exhaust gases in the chamber may be released through the exhaust manifold 726. Further, the flow of exhaust may be controlled by an exhaust valve 728 located within the exhaust manifold 726. As may be readily understood, combustion in the chamber 716 causes the piston 714 to move downward causing rotation of the crankshaft 730. The inertia of a flywheel or combustion in other chambers will cause the crankshaft 730 to rotate further thereby causing a reciprocating motion of the piston 714 upward. The glow plug 724 can be turned on by the ECU 750 through an electrical command 754. The glow plug 724 may also include a sensor 732 to monitor activity within the combustion chamber 716 during the entire cycle of the engine. The sensor 732 may include an ion current sensor with a tube 733 configured to sample gases within the chamber 716. As such, the tube 733 may be in communication with a gas analysis device 735. The sensor signal 734 may be provided to a combustion module 740. The combustion module 740 includes an acquisition module 742 for acquiring the combustion signal and amplifier 744 for enhancing the combustion signal and a signal analysis module 746 to determine certain combustion characteristics based on the enhanced combustion signal. The combustion parameters 748 are then provided to an engine control module 750. The engine control module 750 may then analyze the combustion parameters and control engine operation parameters based on the combustion parameters.

The engine control unit 750 includes a combustion controller 752, a fuel delivery controller 756 and other engine controllers 758. The combustion controller 752 may act as a master module that provides a control signal to different engine components such as the glow plug 724 heater, the fuel delivery system 762, or the injector 722. The fuel delivery controller 756 provides a fuel delivery control signal 760 to an engine fuel delivery system 162. The engine fuel delivery system controls the delivery of fuel to the injector 722. The fuel from the tank 166 is delivered by the fuel pump 164 to the fuel delivery system 762. The fuel delivery system 762 distributes the supplied fuel based on a signal 760 from the ECU 750. The fuel is further supplied to the injector 722 through a fuel line 768. In addition, the fuel delivery controller 756 is in communication electronically with the fuel injector 722 to control different injection parameters such as number of injection events, injection duration and timing as noted by line 770. In addition, the other engine controllers 758 control other engine parameters such as engine speed, load, amount of exhaust gas recirculation, variable geometry turbocharger, or other units installed to the engine. Further, an output sensor 780 may be in communication with the crankshaft 730 to measure crank shaft position, and engine speed, torque of the crankshaft, or vibration of the crank shaft, and provide the feedback signal to the engine control unit 750 as denoted by line 782.

Figure 10:
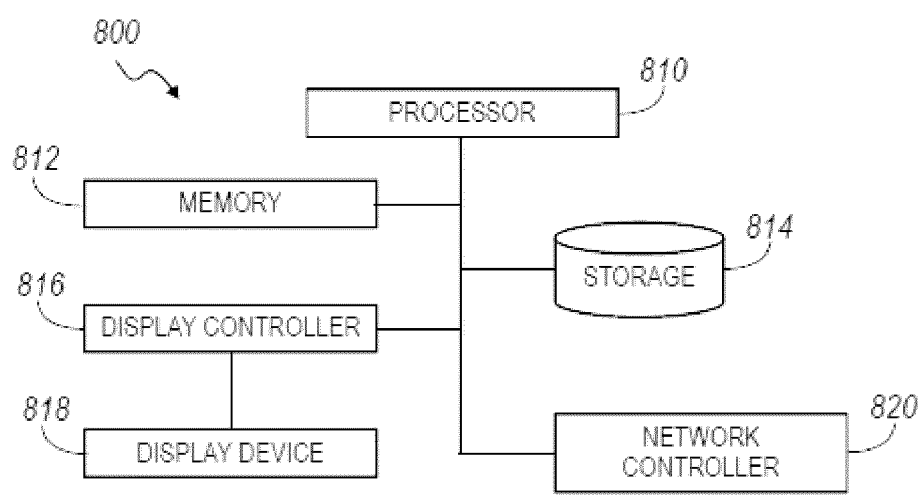
FIG. 10 is a flow chart of a method for managing the data storage and processing the ion current and gas sampled data.

Any of the controllers, circuits, processors, modules, servers, or data processing described may be implemented in one or more computer systems or integrated controllers. One exemplary system is provided in FIG. 10. The computer system 800 includes a processor 810 for executing instructions such as those described in the methods discussed above. The instructions may be stored in a computer readable medium such as memory 812 or storage devices 814, for example a disk drive, CD, or DVD, or in some form of nonvolatile memory, internal or external to the processor, such as EPROM or flash. The computer may include a display controller 816 responsive to instructions to generate a textual or graphical display on a display device 818, for example a computer monitor. In addition, the processor 810 may communicate with a network controller 820 to communicate data or instructions to other systems, for example other general computer systems. The network controller 820 may communicate over Ethernet or other known protocols to distribute processing or provide remote access to information over a variety of network topologies, including local area networks, wide area networks, the Internet, or other commonly used network topologies.

In other embodiments, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit.

Accordingly, the present system encompasses software, firmware, and hardware implementations.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionality as described herein.

Further, the methods described herein may be embodied in a computer-readable medium. The term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

As a person skilled in the art will readily appreciate, the above description is meant as an illustration of the principles of this invention. This description is not intended to limit the scope or application of this invention in that the invention is susceptible to modification, variation and change, without departing from spirit of this invention, as defined in the following claims.

We claim:

1. A probe for gas sampling and ionization sensing, the probe comprising a tube having a first end exposed within a combustion chamber, the first end having an opening configured to receive gas from the combustion chamber and transfer the gas through the tube to a gas analyzer, a sleeve being located around the tube, an electric insulator being located between the sleeve and the tube, where an ion current measuring circuit is connected to the tube and the sleeve such that the electric insulator allows an ion current signal on one of the sleeve or tube to be electrically insulated from a voltage source of the ion current measuring circuit, wherein an opening of the tube is co-located with an ion current measuring surface within the combustion chamber to provide simultaneous measurement of ion current by the ion current measuring circuit and gas analysis by the gas analyzer.

2. The probe of claim 1, wherein the ion current measuring circuit includes an electrical power source and a resistor connected between the tube and the sleeve and the ion current measuring circuit measures the ion current passing through the resistor.

3. The probe of claim 1, wherein the electric insulator is a coating in form of ceramic, paint or any material that has high temperature electric insulation.

4. The probe of claim 3, wherein the electric insulator is applied to the tube.

5. The probe of claim 1, wherein the tube and the sleeve are comprised of metal.

6. A probe for gas sampling and ionization sensing, the probe comprising a tube having a first end exposed within a combustion chamber, the first end having an opening configured to receive gas from the combustion chamber and transfer the gas through the tube to a gas analyzer, an electric insulator being located around the tube, where an ion current measuring circuit is connected to the tube and a metal enclosure of a combustion system, such that the electric insulator allows an ion current signal on one of the metal enclosure or tube to be electrically insulated from a voltage source of the ion current circuit, wherein an opening of the tube is co-located with an ion current measuring surface in the combustion chamber to provide simultaneous measurement of ion current by the ion current measuring circuit and gas analysis by the gas analyzer.

7. The probe of claim 6, wherein the ion current measuring circuit includes an electrical power source and a resistor connected between the tube and the metal enclosure of the combustion system and the ion current measuring circuit measures the ion current passing through the resistor.

8. The probe of claim 6, wherein the electric insulator comprises ceramic.

9. The probe of claim 8, wherein the electric insulator is attached to the tube.

10. The probe of claim 6, wherein the tube is comprised of metal.

11. A system that enables gas analyzers to obtain gas samples and additionally measure ionization data, the system comprising:
a probe and an ion current measuring circuit, the probe comprising a tube having a first end exposed within a combustion chamber, the first end having an opening configured to receive gas from the combustion chamber and transfer the gas through the tube to a gas analyzer, a sleeve being located around the tube, an electric insulator being located between the sleeve and the tube, where the ion current measuring circuit is connected to the tube and the sleeve such that the electric insulator allows an ion current signal on one of the sleeve or tube to be electrically insulated from a voltage source of the ion current measuring circuit, wherein the opening of the tube is co-located with an ion current measuring surface within the combustion chamber to provide simultaneous measurement of the ion current by the ion current measuring circuit and gas analysis by the gas analyzer.

12. The system of claim 11, further comprising a processing unit in communication with the ion current measuring circuit and the gas analyzer, the processing unit being configured to receive simultaneously acquired ion current data from the ion current sensing circuit and a gas analysis data from the gas analyzer.

13. The system of claim 11, wherein the processing unit is configured to synchronize the ion current data and the gas analysis data.

14. The system of claim 11, further comprising a processing unit in communication with the ion current measuring circuit and the gas analyzer, the processing unit being configured to control operating parameters based on an ion current measurement from the ion current sensing circuit and a gas analysis measurement from the gas analyzer.

15. A method for performing simultaneous ionization sensing and gas sampling, the method comprising the steps of:
sensing ionization through a gas sampling probe having electric conductivity, the gas sampling probe having a tube, a sleeve and an electrical insulator, the electric insulator allowing an ion current signal on one of the sleeve or tube to be electrically insulated from a voltage source of an ion current measuring circuit;
sampling the gas at a same location in a combustion chamber as ion current sensing of the probe using the tube;
analyzing the gas provided by the tube using a gas analyzer simultaneously with the ion current sensing.

16. The method of claim 15, further comprising the step of providing a potential to the conductive probe.

17. The method of claim 15, wherein the ionization is measured by an ion current circuit to produce ion current data and the gas sampled to the gas analyzer produces gas analysis data, further comprising the step of synchronizing the ion current data and the gas analysis data.

18. The method of claim 15, wherein the steps of determining ion current and analyzing the gas are performed concurrently.

19. In a non-transitory computer readable storage medium having stored therein instructions executable by a programmed processor for performing ion current measurement and gas analysis, the storage medium comprising instructions for:
  determining ion current through a gas with a conductive probe, the conductive probe having a tube, a sleeve and an electrical insulator, the electric insulator allowing an ion current signal on one of the sleeve or tube to be electrically insulated from a voltage source of an ion current measuring circuit;
  sampling the gas at a same location as ion current sensing of the conductive probe;
  analyzing the gas using a gas analyzer simultaneously with the ion current sensing.

20. The non-transitory computer readable storage medium of claim 19, wherein the ion current is analyzed by an ion current circuit to produce ion current data and the gas analyzer produces gas analysis data, further comprising the step of synchronizing the ion current data and the gas analysis data.

\* \* \* \* \*